(12) United States Patent
Chacon, Jr.

(10) Patent No.: US 11,700,920 B2
(45) Date of Patent: Jul. 18, 2023

(54) HYGIENE MAINTENANCE WRISTBAND

(71) Applicant: Bernardo Garu Chacon, Jr., Hollywood, FL (US)

(72) Inventor: Bernardo Garu Chacon, Jr., Hollywood, FL (US)

(*) Notice: Subject to any disclaimer, the term of this patent is extended or adjusted under 35 U.S.C. 154(b) by 0 days.

(21) Appl. No.: 17/393,911

(22) Filed: Aug. 4, 2021

(65) Prior Publication Data

US 2021/0361036 A1 Nov. 25, 2021

Related U.S. Application Data

(63) Continuation-in-part of application No. 16/781,862, filed on Feb. 4, 2020, now Pat. No. 11,096,528.

(60) Provisional application No. 62/800,986, filed on Feb. 4, 2019.

(51) Int. Cl.
  *A44C 5/00* (2006.01)
  *A47K 5/12* (2006.01)

(52) U.S. Cl.
  CPC .......... *A44C 5/0007* (2013.01); *A47K 5/1201* (2013.01); *A47K 5/1202* (2013.01)

(58) Field of Classification Search
  CPC .... A47K 5/1201; A47K 5/1217; G06F 1/163; A44C 5/0007; A44C 5/003
  See application file for complete search history.

(56) References Cited

U.S. PATENT DOCUMENTS

| | | | |
|---|---|---|---|
| 2,235,350 A | 3/1941 | Violet | |
| 6,415,960 B1 | 7/2002 | Fink et al. | |
| 7,135,011 B2 | 11/2006 | Powers et al. | |
| 7,316,332 B2 | 1/2008 | Powers et al. | |
| 9,578,935 B2* | 2/2017 | Horgan | A45D 34/00 |
| 10,028,624 B1* | 7/2018 | Robinson | A47K 5/1202 |
| 2006/0289567 A1* | 12/2006 | Shoham | A61B 90/80 |
| | | | 222/183 |
| 2008/0067193 A1* | 3/2008 | Powers | A47K 5/122 |
| | | | 222/494 |
| 2009/0008411 A1* | 1/2009 | Schumacher | A01M 1/2033 |
| | | | 222/175 |
| 2011/0155765 A1* | 6/2011 | Properzi | A47K 5/1201 |
| | | | 222/401 |

(Continued)

FOREIGN PATENT DOCUMENTS

BE 896577 A 8/1983
EP 0576629 A4 2/1994

*Primary Examiner* — Vishal Pancholi (57) ABSTRACT

A hygiene maintenance wristband is an apparatus that allows a user to easily maintain the hygiene while on-the-go. The apparatus includes a band, a first casing, a second casing, a solution dispenser, a light mechanism, and a clasp mechanism. The band attaches the first casing and the second casing around the wrist of a user. The first casing houses the solution dispenser. The clasp mechanism is integrated within the second casing in order to connect and disconnect the band. The clasp mechanism also adjusts the overall length of the band around a wrist with a ratchet mechanism. The apparatus further includes a dispenser-release mechanism so that the solution dispenser may be released from the first casing. The light mechanism illuminates as well as identifies germs and bacteria. The apparatus further includes a floss-dispensing mechanism in order to maintain oral hygiene.

19 Claims, 7 Drawing Sheets

(56) References Cited

U.S. PATENT DOCUMENTS

| | | | |
|---|---|---|---|
| 2012/0138637 A1* | 6/2012 | Ciavarella | A44C 15/002 224/148.4 |
| 2012/0282011 A1* | 11/2012 | Francois | A61L 2/18 401/196 |
| 2014/0230960 A1 | 8/2014 | Ciavarella et al. | |
| 2017/0156454 A1* | 6/2017 | Abadi | A44C 5/0053 |
| 2018/0192832 A1* | 7/2018 | Shaukat | A47K 5/1204 |

* cited by examiner

HYGIENE MAINTENANCE WRISTBAND

The current application is a continuation-in-part (CIP) application of a U.S. non-provisional application Ser. No. 16/781,862 filed on Feb. 4, 2020. The U.S. non-provisional application Ser. No. 16/781,862 claims a priority to a U.S. provisional application Ser. No. 62/800,986 filed Feb. 4, 2019.

FIELD OF THE INVENTION

The present invention generally relates to hygiene tools. More specifically, the present invention is a hygiene maintenance wristband.

BACKGROUND OF THE INVENTION

In present times, individuals are known to use a plethora of unique chemical compounds in their lives. Lotions, ointments, atomized perfumes, repellants, sanitizers, etc. are all commonly deployed from their respective containers on a daily basis. Even dental care has been made portable, with small brushed and travel-sized toothpaste tubes being commonly found in bags of travelers, pockets, and purses. With the endless number of compounds that an individual may wish to carry and use on a daily basis, it quickly becomes apparent that they may not all be carried on one's person. The sheer volume of retail-sized containers carrying such a variety of products would quickly fill an entire backpack, if not more. It may similarly be impractical to simply buy "travel-size" containers of such products, given the added expense and absolute unavailability of such packaging for many aerosol products. Additionally, the need to cycle through such a wide variety of possible applicable substance is time consuming and unwieldly, discouraging their use altogether.

The present invention aims to allow a user to carry and deploy an unlimited variety of semi-solid, liquid, gelatinous, or atomized products by re-sealing said products inside a dedicated storage and deployment solution. The present invention will enable users to quickly and directly deploy said compounds to target areas via a wearable watch-type device that can carry and deploy multiple different compounds interchangeably. A means of reloading the expended components of the present invention via a universal tool suitable for attachment to any known retail-size container, in addition to a carrying case, dedicated refill tool, and a variety of possible storage solutions are contemplated.

DETAIL DESCRIPTIONS OF THE INVENTION

All illustrations of the drawings are for the purpose of describing selected versions of the present invention and are not intended to limit the scope of the present invention.

The present invention is a hygiene maintenance wristband that deploys a variety of hygiene solutions that maintain personal hygiene. The present invention is refillable, and the solutions are interchangeable. The present invention is preferably worn around the wrist for quick and easy accessibility. In order for the present invention to be worn around the wrist while comfortably supply a variety of hygiene solutions the present invention comprises a band 1, a first casing 7, a second casing 10, a light mechanism 42, a solution dispenser 13, and a clasp mechanism 26, seen in FIG. 1 and FIG. 2. The band 1 wraps the first casing 7 and the second casing 10 around the wrist of the user. Furthermore, the band 1 comprises a fixed member 2 and an adjustable member 3. The fixed member 2 keeps the first casing 7 and the second casing 10 connected with each other. The adjustable member 3 changes the length of the overall band 1 with the clasp mechanism 26 in order to accommodate various sized wrists. The first casing 7 retains the solution dispenser 13, and the second casing 10 houses the clasp mechanism 26. The first casing 7 and the second casing 10 are both preferably waterproof. The light mechanism 42 illuminates an area for the application of a hygiene solution for easy viewing of nearby objects and any germs on the skin of the user. The solution dispenser 13 houses hygiene solution which may include, but is not limited to, topical skin creams, hand sanitizer, perfume, cologne, and lotions. The clasp mechanism 26 attaches the adjustable member 3 with the second casing 10 and accommodates the lengthening and shortening of the adjustable member 3.

The overall arrangement of the aforementioned components allows the present invention to deploy a variety of hygiene solutions while being worn around the wrist. A first end 4 of the adjustable member 3 and a first end 4 of the fixed member 2 are fixed with the first casing 7, thereby integrating the first casing 7 into the band 1, seen in FIG. 1 and FIG. 2. The band 1 is continuous around the wrist of the user as the first end 4 of the adjustable member 3 is positioned opposite the first end 4 of the fixed member 2 about the first casing 7. A second end 5 of the fixed member 2 is connected with the second casing 10, thereby integrating the second casing 10 into the band 1. The wrist of the user may be placed within the band 1 as the second end 5 of the adjustable member 3 is operatively coupled with the second casing 10 by the clasp mechanism 26, wherein the clasp mechanism 26 is used to readily connect or readily disconnect the adjustable member 3 to the second casing 10. Moreover, the clasp mechanism 26 is used to lengthen or shorten a combined circumference of the band 1, thereby serving as a universal hygiene tool for a variety of users. In order for the band to be secured around the wrist of the user, the second end 5 of the adjustable member 3 is positioned opposite the second end 5 of the fixed member 2 about the second casing 10. As the palm of the hand is positioned adjacent with the first casing, the solution dispenser 13 is integrated into the first casing 7. This allows the solution to be directly released onto the palm of the user, the surface of the hand that receives the most contact with germs. Similarly, in order to project light onto any desired surface, the light mechanism 42 is integrated into the second casing 10.

Figure 1:
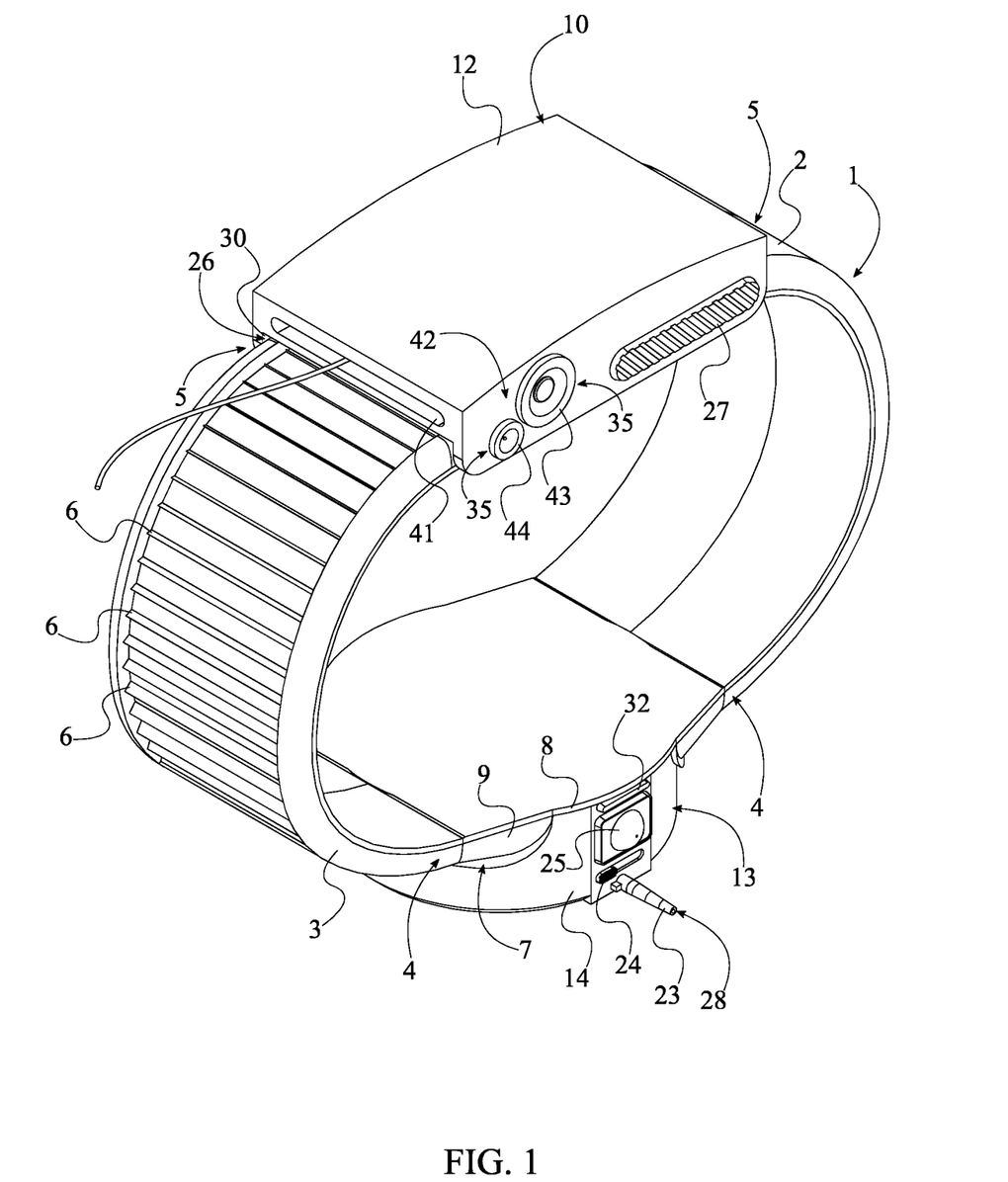
FIG. 1 is a top perspective view of the preferred embodiment of the present invention with a portable computing device integrated with a second casing.
Figure 2:
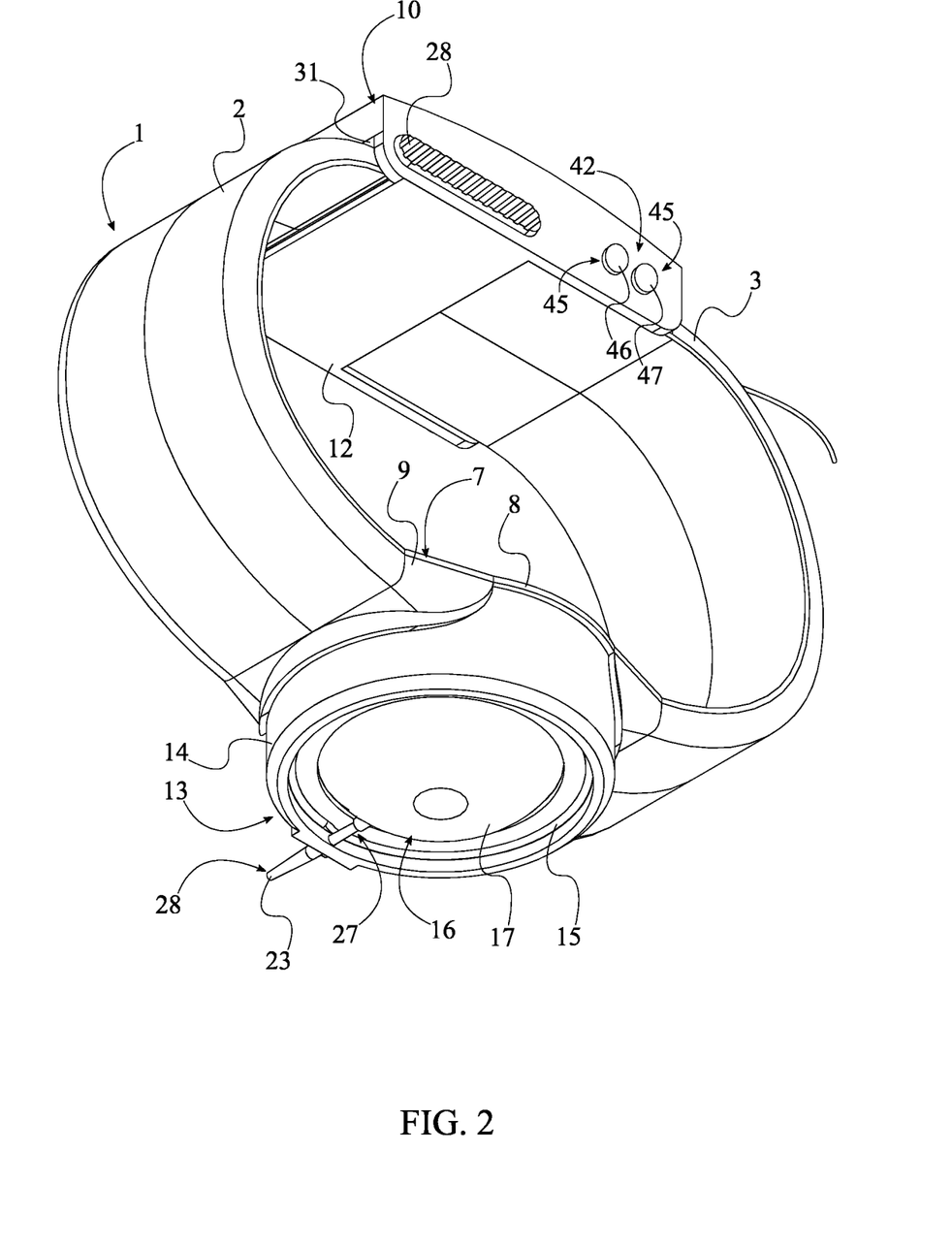
FIG. 2 is a bottom perspective view of the preferred embodiment of the present invention with the portable computing device integrated with the second casing.

This allows the light emitted by the light mechanism 42 to remain uninhibited by the hand of the user regardless of the position or motion of the hand.

Figure 5:
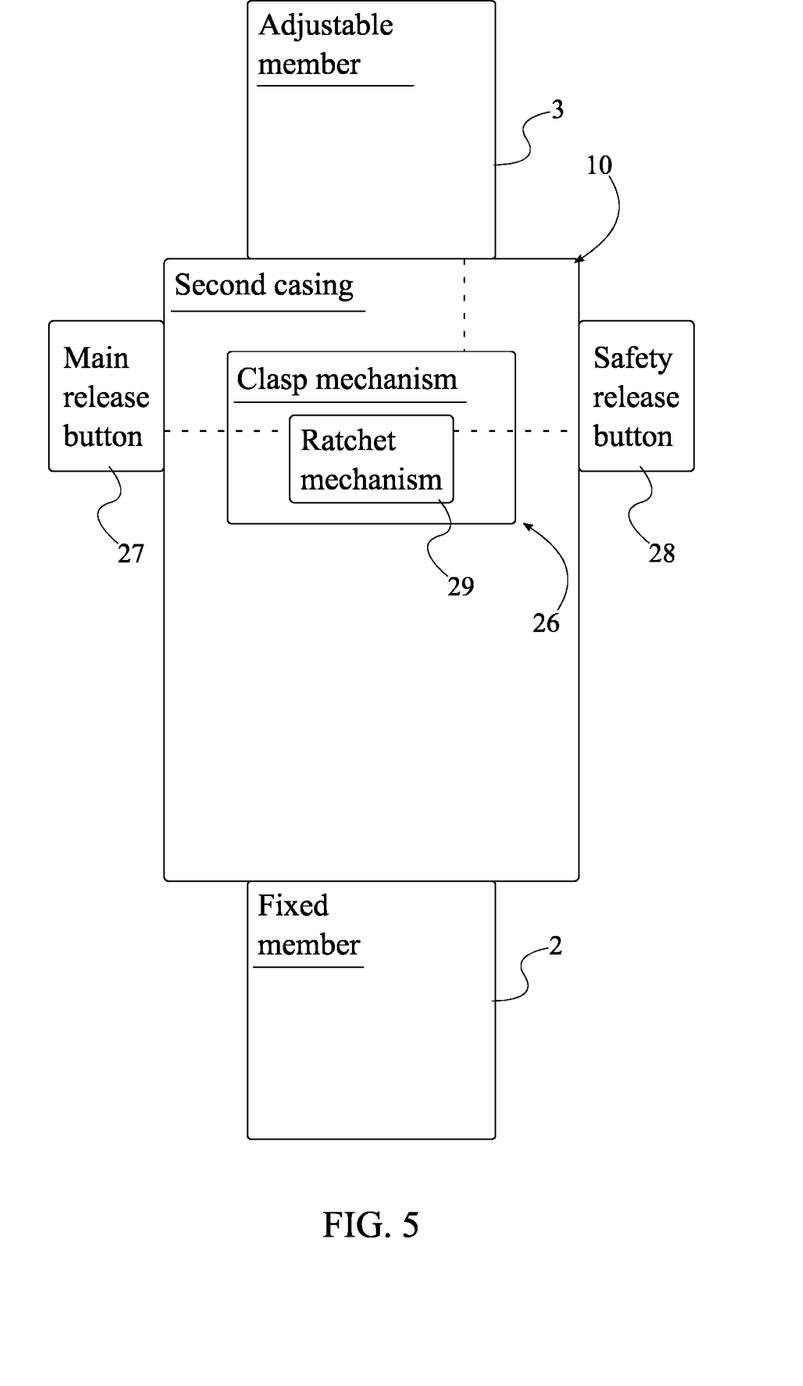
FIG. 5 is a schematic view of a clasp mechanism of the present invention.
Figure 6:
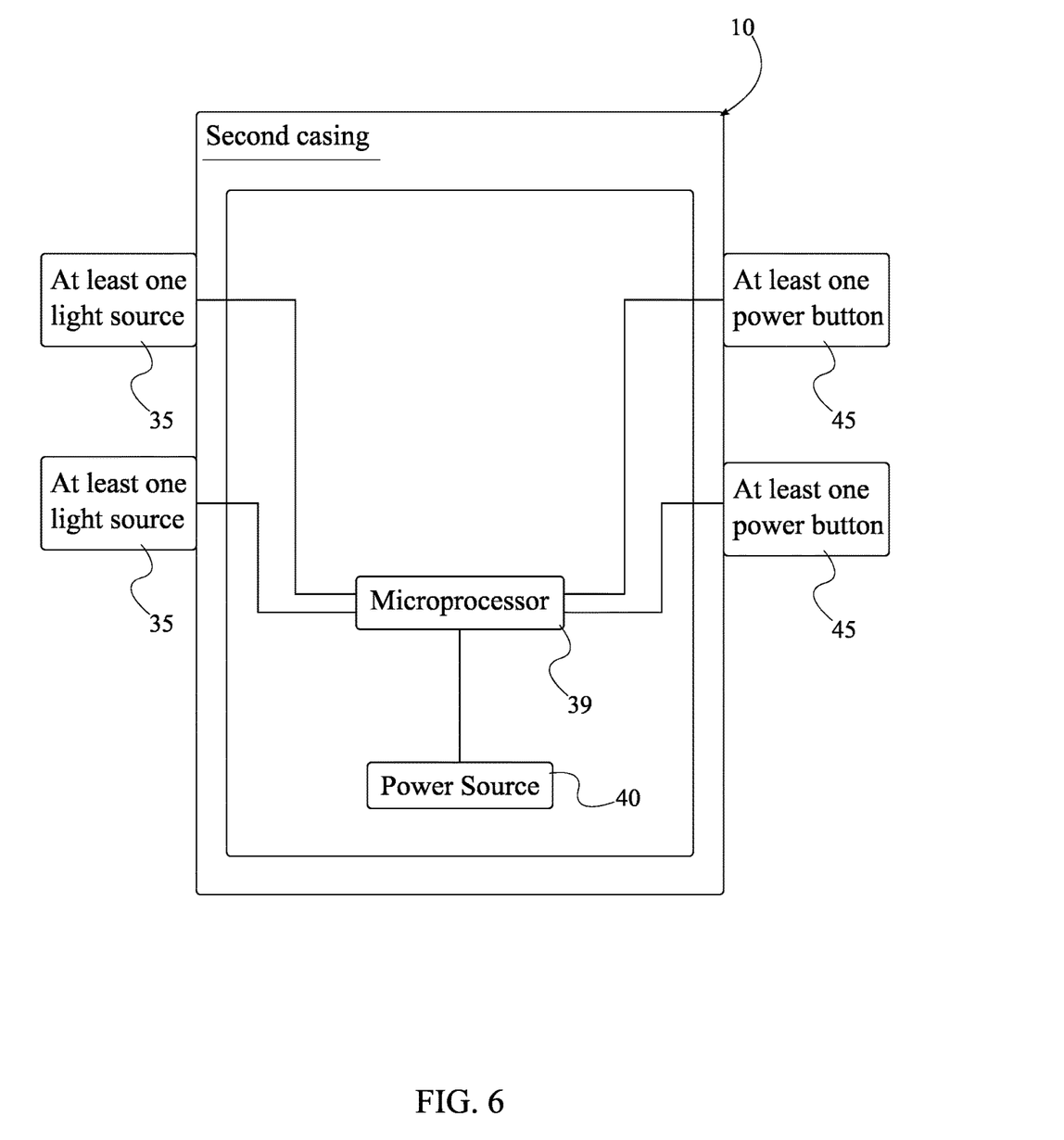
FIG. 6 is a schematic view of the electronic connections of the present invention.
Figure 7:
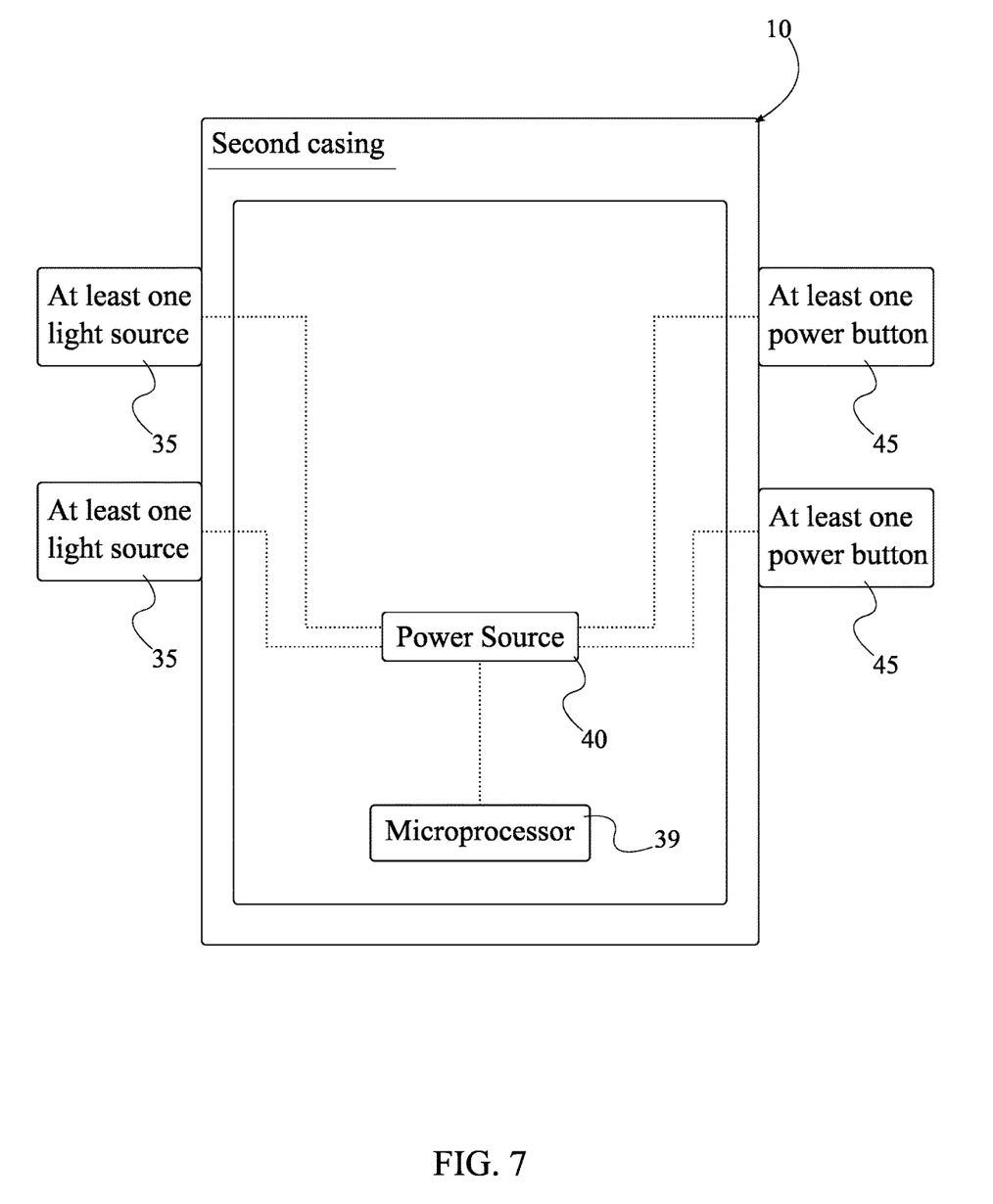
FIG. 7 is a schematic view of the electrical connections of the present invention.

In order for the clasp mechanism 26 to provide a secure connection between the adjustable member 3 and the second casing 10 while being able to vary the combined circumference of the band 1, the clasp mechanism 26 comprises a main release button 27, a safety release button 28, a ratchet mechanism 29, a first slot 30, and a second slot 31, seen in FIG. 1, FIG. 2, and FIG. 5. The main release button 27 and the safety release button 28 allows only the purposeful separation of the adjustable member 3 with the second casing 10. The ratchet mechanism 29 allows for the combined circumference to be adjusted. The adjustable member 3 is engaged with the ratchet mechanism 29 through the first slot 30, and the fixed member 2 is secured within the second casing 10 through the second slot 31. In order for the adjustable member 3 to be secured with the ratcheting mechanism, the band 1 comprises a plurality of tracks 6. The plurality of tracks 6 secures the adjustable member 3 with the second casing 10 for any size of the combined circumference of the band 1. The adjustable member 3 defines the combined circumference of the band 1 as the plurality of tracks 6 is integrated along the adjustable member 3. The main release button 27 and the safety release button 28 are positioned opposite each other about the second casing 10 in order to require the second casing 10 to be pressed along both sides to release the ratchet mechanism 29. The main release button 27 and the safety release button 28 are easily accessible by a user as the main release button 27 and the safety release button 28 are externally integrated into the second casing 10. The first slot 30 laterally traverses into the second casing 10, and the second slot 31 laterally traverses into the second casing 10, opposite the first slot 30 so that the band 1 is continuous around the wrist of the user. The second end 5 of the fixed member 2 is connected within the second slot 31. A wrist is easily positioned and secured within the band 1 as the second end 5 of the adjustable member 3 is operatively coupled within the first slot 30 by an engagement between the ratchet mechanism 29 and the plurality of tracks 6, wherein the ratchet mechanism 29 is used to readily engage or readily disengage the plurality of tracks 6. The main release button 27 and the safety release button 28 are operatively coupled with the ratchet mechanism 29, wherein the main release button 27 and the safety button are simultaneously pressed in order to release the ratchet mechanism 29. This engagement serves as a safety lock between the adjustable member 3 and the second casing 10.

Figure 3:
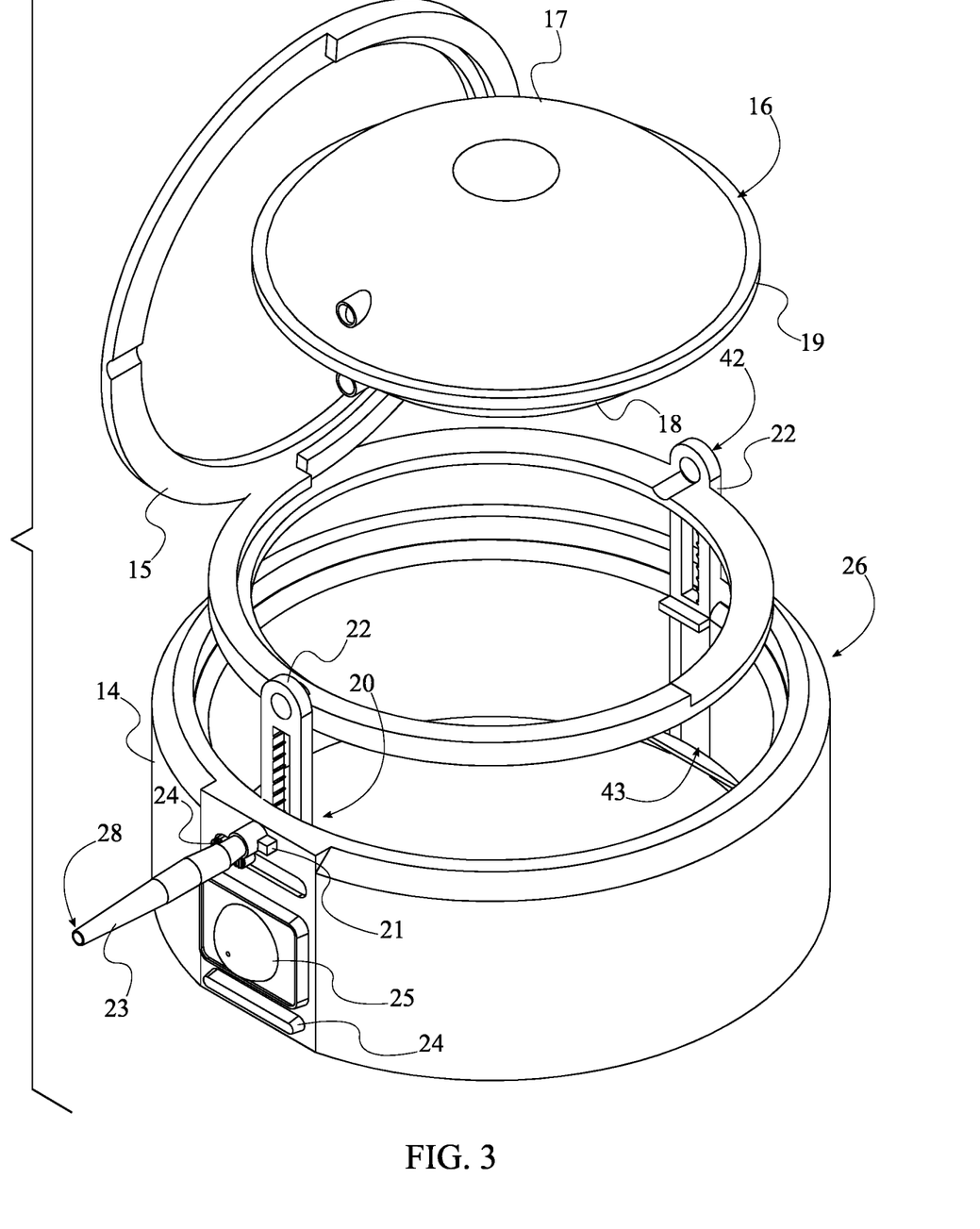
FIG. 3 is an exploded view of a solution dispenser of the present invention.
Figure 4:
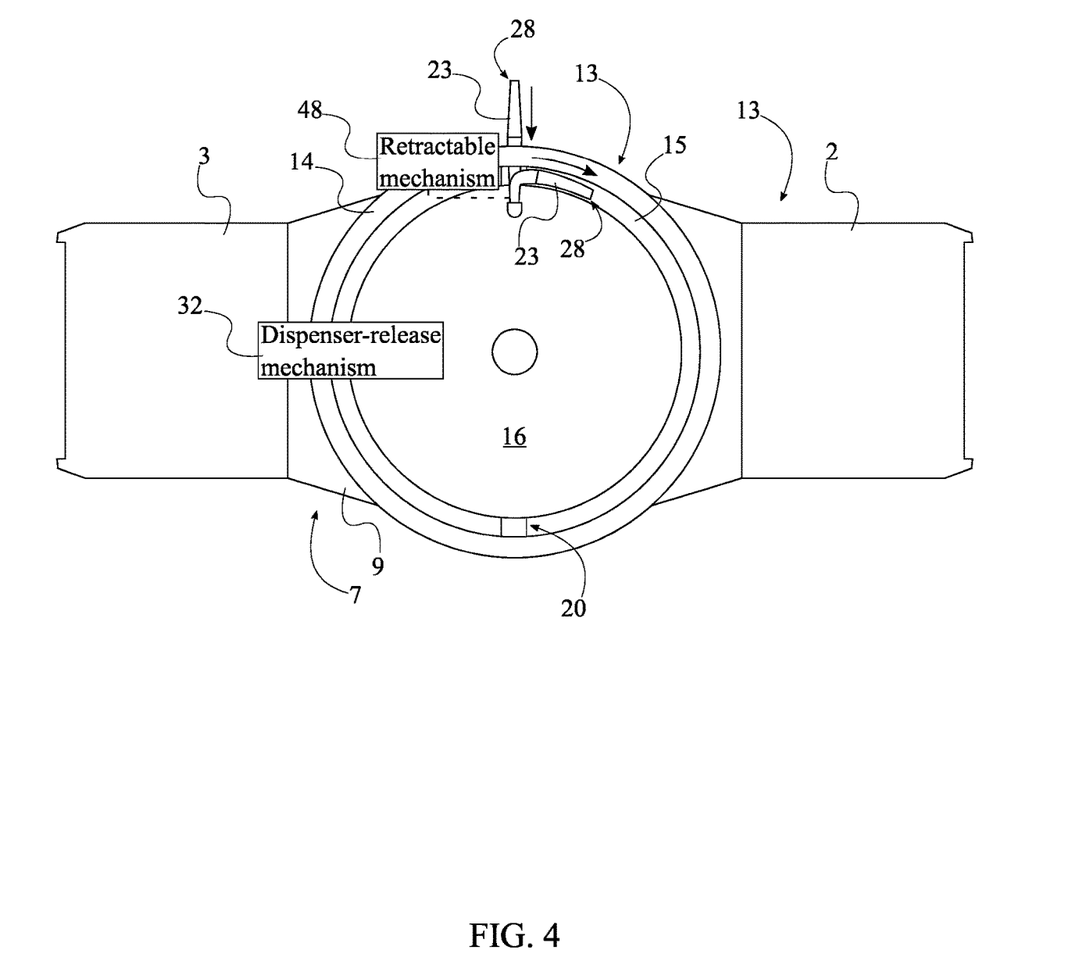
FIG. 4 is a schematic view of a retracting mechanism and a dispenser-release mechanism of the present invention.

In order for the solution dispenser 13 to be securely housed within the first casing 7 and be readily separated from the first casing 7, the present invention comprises a dispenser-release mechanism 32, seen in FIG. 4. In the preferred embodiment of the present invention, the dispenser-release mechanism 32 is a snap lock. The first casing 7 also comprises a base wall 8 and a lateral wall 9, seen in FIG. 1 and FIG. 2. The base wall 8 connects the adjustable member 3 and the fixed member 2 with the first casing 7. The lateral wall 9 surrounds the solution dispenser 13 and houses the dispenser-release mechanism 32. The solution dispenser 13 further comprises a frame 14, an annular retainer 15, and at least one pod 16, seen in FIG. 1, FIG. 2, and FIG. 3. The frame 14 houses the annular retainer 15 and the at least one pod 16 within the solution dispenser 13. The annular retainer 15 secures the at least one pod 16 within the frame 14. The at least one pod 16 contains a hygiene solution. The base wall 8 is positioned adjacent with the lateral wall 9, and the lateral wall 9 is perimetrically fixed around the base wall 8 in order to effectively house the solution dispenser 13 when connected with the first casing 7. The frame 14 is positioned within the lateral wall 9, and the annular retainer 15 is mounted onto the frame 14 and is removably attached around the at least one pod 16. This arrangement allows the entire solution dispenser 13 to be separated from the first casing 7. The solution dispenser 13 is securely attached within the first casing 7 and is easily separated as the frame 14 is operatively coupled with the lateral wall 9 by the dispenser-release mechanism 32, wherein the dispenser-release mechanism 32 is used to lock or unlock the frame 14 with the lateral wall 9. The solution dispenser 13 may be engaged while disconnected from the first casing 7.

The solution dispenser 13 further comprises a pod-releasing mechanism 20, a nozzle 23, a retracting mechanism 48, and a release switch 24 in order remove or access the at least one pod 16 positioned within the frame 14, also seen in FIG. 1, FIG. 2, FIG. 3, and FIG. 4. The pod-releasing mechanism 20 retracts and ejects the at least one pod 16. In the preferred embodiment of the present invention, the pod-releasing mechanism 20 is automatic. The nozzle 23 dispenses the hygiene solution contained within the nozzle 23. Moreover, the nozzle 23 serves as a latch or lock for the pod-releasing mechanism 20. The retracting mechanism 48 automatically maneuvers the nozzle 23 into and out of the frame 14 so that the nozzle 23 is safely stored within the frame 14 while not in use. The release switch 24 allows a user to manually operate the pod-releasing mechanism 20. In order for the at least one pod 16 to be secured with the frame 14, the annular retainer 15 is attached around the at least one pod 16. In order for the solution within the at least one pod 16 to traverse into the nozzle 23, a first end 27 of the nozzle 23 is in fluid communication with the at least one pod 16. The first end 27 provides a continuous and free path for the solution to enter the nozzle 23 and serves as an inlet for the nozzle 23. The nozzle 23 is integrated through the frame 14, thereby allowing the solution to traverse through the frame 14. The solution is released from the nozzle 23 and directly onto the palm of the user as a second end of the nozzle 23 is externally positioned with the frame 14. The second end 28 serves as an outlet for the nozzle 23. The annular retainer 15 is operatively coupled to the frame 14 by the pod-releasing mechanism 20, wherein the pod-releasing mechanism 20 is used to extend the frame 14 out of the second casing 10 and is used to then rotate the annular retainer 15, thereby facilitating the access of the at least one pod 16. The release switch 24 is operatively coupled to the pod-releasing mechanism 20, wherein the release switch 24 is used to actuate the pod-releasing mechanism 20 so that the user simply engages the release switch 24 to access the at least one pod 16. In the preferred embodiment of the present invention, the at least one pod 16 with the annular retainer 15 is retracted into frame 14 with a simple push of the annular retainer 15 to again active the pod-releasing mechanism 20. It is understood that various embodiments of the present invention may further comprises a switch that automatically retracts the at least one pod 16 with the annular retainer 15 back into the frame 14. In order for the nozzle to be automatically engaged by the user, the nozzle 23 is operatively coupled to the frame 14 by the retracting mechanism 48, wherein the retraction mechanism 48 is used to extend the nozzle 23 out of the frame 14 and is used to retract the nozzle 23 into the frame 14. In order to maintain the compact and ergonomic structure of the present invention, the nozzle 23 is flexible.

This arrangement protects the nozzle 23 from accidently getting snagged and breaking while not being used to dispense hygiene solution.

In order to automatically access the at least one pod 16, the pod-releasing mechanism 20 comprises a control button 21 and a couple of rail assemblies 22, seen in FIG. 3. The control button 21 activates the couple of rail assemblies 22, and the couple of rail assemblies 22 slide the annular retainer 15 into and out of the frame 14. Each of the couple of rail assemblies 22 comprises a stopper end 42 and a rotation end 43. The stopper end 42 prevents the annular retainer 15 from retracting through the frame 14, and the rotation end 43 is the rotation axis for the annular retainer 15. The stopper end 42 is positioned opposite the rotation end 43 along the rail assembly in order for the annular retainer 15 to freely and continuously rotate. More specifically, the annular retainer 15 is rotatably mounted with the rotation end 43. The control button 21 is externally mounted with the frame 14, allowing a user to engage with the control button 21. The at least one pod 16 exits and enters the frame 14 with the annular retainer 15 as the at least one pod 16 is slidably engaged along the couple of rail assemblies 22. The pod-releasing mechanism 20 is automatic as control button 21 is operatively coupled to the rotation end 43 of each of the couple of rail assemblies 22, wherein the control button 21 is used to actuate the rotation end 43 and is consequently used to flip the at least one pod 16.

Before the application of any hygiene solution within the at least one pod 16, the surface or area may be checked for any germs or bacteria as the solution dispenser 13 further comprises a bacteria-detecting light source 25, seen in FIG. 1 and FIG. 3. The bacteria-detecting light source 25 is preferably a blacklight, however, alternate embodiments of the bacteria-light source may be an ultraviolet light. The bacteria-detecting light source 25 is externally integrated with the frame 14 effectively illuminating a desired area positioned adjacent the nozzle 23.

The at least one pod 16 may dispense more than one hygiene solution as the at least one pod 16 comprises a first retaining portion 17, a second retaining portion 18, and a disk plate 19, seen in FIG. 3. The first retaining portion 17 and the second retaining portion 18 each contain hygiene solutions that are preferably different from one another. The disk plate 19 connects the first retaining portion 17 with the second retaining portion 18. The first retaining portion 17 is mounted onto the disk plate 19. The second retaining portion 18 is mounted onto the disk plate 19, opposite the first retaining portion 17. This arrangement allows the nozzle 23 to engage with both the first retaining portion 17 and the second retaining portion 18 upon the engagement of the pod-releasing mechanism 20.

In alternate embodiments of the present invention, a spray nozzle may be mounted adjacent the nozzle 23, opposite the at least one pod 16. The spray nozzle evenly distributed a hygiene solution as a spray. The hygiene solution is preferably perfume or cologne. In further embodiments of the present invention, the at least one pod 16 is refillable. The at least one pod 16 is preferably refilled with a solution pen that comprises a reservoir of hygiene solution. The solution pen refills the at least one pod 16 through the second end 28 of the nozzle 23. In further embodiments of the present invention, the at least one pod 16 with a first retaining portion 17 and a second retaining portion 18 further comprises a first identifying marker and a second identifying marker. The first identifying marker labels the first retaining portion 17 with the hygiene solution within the first retaining portion 17. Similarly, the second identifying marker labels the second retaining portion 18 with hygiene solution within the second retaining portion 18.

In the preferred embodiment of the present invention, the light mechanism 42 comprises at least one light source 35, at least one power button 45, a microprocessor 39, and a power source 40, seen in FIG. 1, FIG. 2, FIG. 6, and FIG. 7. The at least one light source 35 emits light onto the hand of the user or a desired surface. The at least one power button 45 turns off and turns on the at least one light source 35. The microprocessor 39 manages the function of the at least one light source 35. The power source 40 provides the necessary power for the at least one light source 35 and the microprocessor 39 to operate. The power source 40 may be recharged with an external power supply. Furthermore, in the preferred embodiment of the present invention, the second casing comprises a first flat surface 11 and a second flat surface 12. The first flat surface 11 is exposed to the surrounding environment of the present invention. The second flat surface 12 presses against the skin of the user. Moreover, the first flat surface 11 is positioned opposite the second flat surface 12 about the second casing 10, and the second flat surface 12 is oriented towards the first casing 7. In order for the light emitted by the at least one light source 35 to remain uninhibited and the at least one power source 40 to remain accessible by the user, the at least one light source 35 and the at least one power button 45 are laterally mounted with the second casing 10 in between the first flat surface 11 and the second flat surface 12. More specifically, the at least one light source 35 is positioned opposite the at least one power button 45 about the second casing 10 facilitating the engagement of the at least one power button 45 by the user. The microprocessor 39 and the power source 40 are mounted within the second casing 10, thereby housing and protecting the microprocessor 39 and the power source 40. The at least one light source 35 is operable by the at least one power button 45 as the microprocessor 39 is electronically connected with the at least one light source 35, the at least one power button 45, and the power source 40. The power source 40 is electrically connected with the at least one light source 35, the at least one power button 45, and the microprocessor 39, thereby supplying the at least one light source 35 and the microprocessor 39 with the necessary power.

Furthermore, in the preferred embodiment of the present invention, the at least one light source 35 comprises a main light source 43 and a supplementary bacteria-detecting light source 44, seen in FIG. 1 and FIG. 2. The main light source 43 illuminates a desired area nearby the present invention. More specifically, the main light source 43 illuminates the topside of the hand of the user. The supplementary bacteria-detecting light source 44 identifies germs and bacteria of a desired surface for application such as the palm of the hand of the user. In order to operate the main light source 43 and the supplementary bacteria-detecting light source 44, the at least one power button 45 comprises a first power button 46 and a second power button 47. The first power button 46 controls the main light source 43, and the second power button 47 controls the supplementary bacteria-detecting light source 44. Both the main light source 43 and the supplementary bacteria-detecting light source 44 provide optimal illumination for a desired surface as the main light source 43 and the supplementary bacteria-detecting light source 44 are positioned adjacent with each other. Both the first power button 46 and the second power button 47 are easily accessible by the user as the first power button 46 and the second power button 47 are positioned adjacent with each other. The main light source 43 is operatively coupled with the first power button 46 wherein, the first power button 46 is used to turn off and turn on the main light source 43 as the first power button 46 connects and disconnects the connection between the power source 40 and the main light source 43. The supplementary bacteria-detecting light source 44 is operatively coupled with the second power button 47 wherein, the second power button 47 is used to turn off and turn on the supplementary bacteria-detecting light source 44 as the second power button 47 connects and disconnects the connection between the power source 40 and supplementary the bacteria-detecting light source 44.

The preferred embodiment of the present invention further comprises a floss-dispensing mechanism 41 in order to better maintain oral hygiene, seen in FIG. 1. The floss-dispensing mechanism 41 is laterally integrated into the second casing 10 so floss is easily taken from the second casing 10 while the main display screen 34 remains visible and may encompass a larger area across the second casing 10.

Although the invention has been explained in relation to its preferred embodiment, it is to be understood that many other possible modifications and variations can be made without departing from the spirit and scope of the invention as hereinafter claimed.

What is claimed is:

1. A hygiene maintenance wristband comprises:
a band;
a first casing;
a second casing;
a solution dispenser;
a light mechanism;
a clasp mechanism;
a floss-dispensing mechanism;
the band comprises a fixed member and an adjustable member;
a first end of the adjustable member and a first end of the fixed member being fixed with the first casing;
the first end of the adjustable member being positioned opposite the first end of the fixed member about the first casing;
a second end of the fixed member being connected with the second casing;
a second end of the adjustable member being operatively coupled with the second casing by the clasp mechanism, wherein the clasp mechanism is used to readily connect or readily disconnect the adjustable member to the second casing, and wherein the clasp mechanism is used to lengthen or shorten a combined circumference of the band;
the second end of the adjustable member being positioned opposite the second end of the fixed member about the second casing;
the solution dispenser being integrated into the first casing;
the light mechanism being integrated into the second casing; and,
the floss-dispensing mechanism being laterally integrated into the second casing.

2. The hygiene maintenance wristband as claimed in claim 1 comprises:
the clasp mechanism comprises a main release button, a safety release button, a ratchet mechanism, a first slot, and a second slot;
the band comprises a plurality of tracks;
the plurality of tracks being integrated along the adjustable member;
the main release button and the safety release button being positioned opposite each other about the second casing;
the main release button and the safety release button being externally integrated into the second casing;
the first slot laterally traversing into the second casing;
the second slot laterally traversing into the second casing, opposite the first slot;
the second end of the fixed member being connected within the second slot;
the second end of the adjustable member being operatively coupled within the first slot by an engagement between the ratchet mechanism and the plurality of tracks, wherein the ratchet mechanism is used to readily engage or readily disengage the plurality of tracks; and,
the main release button and the safety release button being operatively coupled with the ratchet mechanism, wherein the main release button and the safety button are simultaneously pressed in order to release the ratchet mechanism.

3. The hygiene maintenance wristband as claimed in claim 1 comprises:
a dispenser-release mechanism;
the first casing comprises a base wall and a lateral wall;
the solution dispenser comprises a frame, an annular retainer, and at least one pod;
the base wall being positioned adjacent with the lateral wall;
the lateral wall being perimetrically fixed around the base wall;
the frame being positioned within the lateral wall;
the annular retainer being mounted onto the frame;
the annular retainer being removably attached around the at least one pod; and,
the frame being operatively coupled with the lateral wall by the dispenser-release mechanism, wherein the dispenser-release mechanism is used to lock or unlock the frame with the lateral wall.

4. The hygiene maintenance wristband as claimed in claim 1 comprises:
the solution dispenser comprises a frame, an annular retainer, at least one pod, a pod-releasing mechanism, a nozzle, a retracting mechanism, and a release switch;
the annular retainer being attached around the at least one pod;
a first end of the nozzle being in fluid communication with the at least one pod;
the nozzle being integrated through the frame;
a second end of the nozzle being externally positioned with the frame;
the annular retainer being operatively coupled to the frame by the pod-releasing mechanism, wherein the pod-releasing mechanism is used to extend the frame out of the second casing and is used to then rotate the annular retainer;
the release switch being operatively coupled to the pod-releasing mechanism, wherein the release switch is used to actuate the pod-releasing mechanism; and,
the nozzle being operatively coupled to the frame by the retracting mechanism, wherein the retraction mechanism is used to extend the nozzle out of the frame and is used to retract the nozzle into the frame.

5. The hygiene maintenance wristband as claimed in claim 4 comprises:
the pod-releasing mechanism comprises a control button and a couple of rail assemblies;

each of the couple of rail assemblies comprises a stopper end and a rotation end;
the stopper end being positioned opposite the rotation end along the rail assembly;
the annular retainer being rotatably mounted with the rotation end;
the control button being externally mounted with the frame;
the at least one pod being slidably engaged along the couple of rail assemblies; and,
the control button being operatively coupled to the rotation end of each of the couple of rail assemblies, wherein the control button is used to actuate the rotation end and is consequently used to flip the at least one pod.

6. The hygiene maintenance wristband as claimed in claim 4 comprises:
the nozzle being flexible.

7. The hygiene maintenance wristband as claimed in claim 4 comprises:
the solution dispenser further comprises a bacteria-detecting light source; and,
the bacteria-detecting light source being externally integrated with the frame.

8. The hygiene maintenance wristband as claimed in claim 1 comprises:
the solution dispenser comprises at least one pod;
the at least one pod comprises a first retaining portion, a second retaining portion, and a disk plate;
the first retaining portion being mounted onto the disk plate; and,
the second retaining portion being mounted onto the disk plate, opposite the first retaining portion.

9. The hygiene maintenance wristband as claimed in claim 1 comprises:
the light mechanism comprises at least one light source, at least one power button, a microprocessor, and a power source;
the second casing comprises a first flat surface and a second flat surface;
the first flat surface being positioned opposite the second flat surface about the second casing;
the second flat surface being oriented towards the first casing;
the at least one light source and the at least one power button being laterally mounted with the second casing in between the first flat surface and the second flat surface;
the at least one light source being positioned opposite the at least one power button about the second casing;
the microprocessor and the power source being mounted within the second casing;
the microprocessor being electronically connected with the at least one light source, the at least one power button, and the power source; and,
the power source being electrically connected with the at least one light source, the at least one power button, and the microprocessor.

10. The hygiene maintenance wristband as claimed in claim 9 comprises:
the at least one light source comprises a main light source and a supplementary bacteria-detecting light source;
the at least one power button comprises a first power button and a second power button;
the main light source and the supplementary bacteria-detecting light source being positioned adjacent with each other;
the first power button and the second power button being positioned adjacent with each other;
the main light source being operatively coupled with the first power button wherein, the first power button is used to turn off and turn on the main light source; and,
the supplementary bacteria-detecting light source being operatively coupled with the second power button wherein, the second power button is used to turn off and turn on the supplementary bacteria-detecting light source.

11. A hygiene maintenance wristband comprises:
a band;
a first casing;
a second casing;
a solution dispenser;
a light mechanism;
a clasp mechanism;
the band comprises a fixed member and an adjustable member;
the solution dispenser comprises a frame, an annular retainer, at least one pod, a pod-releasing mechanism, a nozzle, a retracting mechanism, and a release switch;
the light mechanism comprises at least one light source, at least one power button, a microprocessor, and a power source;
a first end of the adjustable member and a first end of the fixed member being fixed with the first casing;
the first end of the adjustable member being positioned opposite the first end of the fixed member about the first casing;
a second end of the fixed member being connected with the second casing;
a second end of the adjustable member being operatively coupled with the second casing by the clasp mechanism, wherein the clasp mechanism is used to readily connect or readily disconnect the adjustable member to the second casing, and wherein the clasp mechanism is used to lengthen or shorten a combined circumference of the band;
the second end of the adjustable member being positioned opposite the second end of the fixed member about the second casing;
the solution dispenser being integrated into the first casing;
the light mechanism being integrated into the second casing;
the annular retainer being attached around the at least one pod;
a first end of the nozzle being in fluid communication with the at least one pod;
the nozzle being integrated through the frame;
a second end of the nozzle being externally positioned with the frame;
the annular retainer being operatively coupled to the frame by the pod-releasing mechanism, wherein the pod-releasing mechanism is used to extend the frame out of the second casing and is used to then rotate the annular retainer;
the release switch being operatively coupled to the pod-releasing mechanism, wherein the release switch is used to actuate the pod-releasing mechanism;
the nozzle being operatively coupled to the frame by the retracting mechanism, wherein the retraction mechanism is used to extend the nozzle out of the frame and is used to retract the nozzle into the frame;
the second casing comprises a first flat surface and a second flat surface;

the first flat surface being positioned opposite the second flat surface about the second casing;

the second flat surface being oriented towards the first casing;

the at least one light source and the at least one power button being laterally mounted with the second casing in between the first flat surface and the second flat surface;

the at least one light source being positioned opposite the at least one power button about the second casing;

the microprocessor and the power source being mounted within the second casing;

the microprocessor being electronically connected with the at least one light source, the at least one power button, and the power source; and, the power source being electrically connected with the at least one light source, the at least one power button, and the microprocessor.

12. The hygiene maintenance wristband as claimed in claim 11 comprises:

the clasp mechanism comprises a main release button, a safety release button, a ratchet mechanism, a first slot, and a second slot;

the band comprises a plurality of tracks;

the plurality of tracks being integrated along the adjustable member;

the main release button and the safety release button being positioned opposite each other about the second casing;

the main release button and the safety release button being externally integrated into the second casing;

the first slot laterally traversing into the second casing;

the second slot laterally traversing into the second casing, opposite the first slot;

the second end of the fixed member being connected within the second slot;

the second end of the adjustable member being operatively coupled within the first slot by an engagement between the ratchet mechanism and the plurality of tracks, wherein the ratchet mechanism is used to readily engage or readily disengage the plurality of tracks; and, the main release button and the safety release button being operatively coupled with the ratchet mechanism, wherein the main release button and the safety button are simultaneously pressed in order to release the ratchet mechanism.

13. The hygiene maintenance wristband as claimed in claim 11 comprises:

a dispenser-release mechanism;

the first casing comprises a base wall and a lateral wall;

the solution dispenser comprises a frame, an annular retainer, and at least one pod;

the base wall being positioned adjacent with the lateral wall;

the lateral wall being perimetrically fixed around the base wall;

the frame being positioned within the lateral wall;

the annular retainer being mounted onto the frame;

the annular retainer being removably attached around the at least one pod; and, the frame being operatively coupled with the lateral wall by the dispenser-release mechanism, wherein the dispenser-release mechanism is used to lock or unlock the frame with the lateral wall.

14. The hygiene maintenance wristband as claimed in claim 11 comprises:

the pod-releasing mechanism comprises a control button and a couple of rail assemblies;

each of the couple of rail assemblies comprises a stopper end and a rotation end;

the stopper end being positioned opposite the rotation end along the rail assembly;

the annular retainer being rotatably mounted with the rotation end;

the control button being externally mounted with the frame;

the at least one pod being slidably engaged along the couple of rail assemblies; and, the control button being operatively coupled to the rotation end of each of the couple of rail assemblies, wherein the control button is used to actuate the rotation end and is consequently used to flip the at least one pod.

15. The hygiene maintenance wristband as claimed in claim 11 comprises:

the nozzle being flexible.

16. The hygiene maintenance wristband as claimed in claim 11 comprises:

the solution dispenser further comprises a bacteria-detecting light source; and, the bacteria-detecting light source being externally integrated with the frame.

17. The hygiene maintenance wristband as claimed in claim 11 comprises:

the solution dispenser comprises at least one pod;

the at least one pod comprises a first retaining portion, a second retaining portion, and a disk plate;

the first retaining portion being mounted onto the disk plate; and, the second retaining portion being mounted onto the disk plate, opposite the first retaining portion.

18. The hygiene maintenance wristband as claimed in claim 11 comprises:

the at least one light source comprises a main light source and a supplementary bacteria-detecting light source;

the at least one power button comprises a first power button and a second power button;

the main light source and the supplementary bacteria-detecting light source being positioned adjacent with each other;

the first power button and the second power button being positioned adjacent with each other;

the main light source being operatively coupled with the first power button wherein, the first power button is used to turn off and turn on the main light source; and, the supplementary bacteria-detecting light source being operatively coupled with the second power button wherein, the second power button is used to turn off and turn on the supplementary bacteria-detecting light source.

19. The hygiene maintenance wristband as claimed in claim 11 comprises:

a floss-dispensing mechanism; and, the floss-dispensing mechanism being laterally integrated into the second casing.

* * * * *